United States Patent
Vasquez

(10) Patent No.: US 10,426,803 B2
(45) Date of Patent: *Oct. 1, 2019

(54) TOPICAL MEDICAMENT FOR SKIN AND MUCOSAL INJURIES

(71) Applicant: REV PHARMA Corp., Miami, FL (US)

(72) Inventor: Efrain Ramon Vasquez, Lujan de Cuyo (AR)

(73) Assignee: REV PHARMA CORP, Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/011,195

(22) Filed: Jun. 18, 2018

(65) Prior Publication Data

US 2018/0296611 A1 Oct. 18, 2018

Related U.S. Application Data

(63) Continuation of application No. 15/525,629, filed as application No. PCT/US2015/060555 on Nov. 13, 2015, now Pat. No. 10,016,466.

(60) Provisional application No. 62/080,786, filed on Nov. 17, 2014.

(51) Int. Cl.
| | |
|---|---|
| *A61K 35/644* | (2015.01) |
| *A61K 9/00* | (2006.01) |
| *A61K 47/06* | (2006.01) |
| *A61K 9/06* | (2006.01) |
| *A61K 31/07* | (2006.01) |
| *A61K 31/355* | (2006.01) |
| *A61K 31/59* | (2006.01) |
| *A61K 36/87* | (2006.01) |
| *A61K 36/537* | (2006.01) |
| *A61K 36/55* | (2006.01) |
| *A61K 36/63* | (2006.01) |
| *A61K 35/06* | (2006.01) |
| *A61K 47/10* | (2017.01) |
| *A61P 17/00* | (2006.01) |

(52) U.S. Cl.
CPC .......... *A61K 35/644* (2013.01); *A61K 9/0014* (2013.01); *A61K 9/06* (2013.01); *A61K 31/07* (2013.01); *A61K 31/355* (2013.01); *A61K 31/59* (2013.01); *A61K 35/06* (2013.01); *A61K 36/537* (2013.01); *A61K 36/55* (2013.01); *A61K 36/63* (2013.01); *A61K 36/87* (2013.01); *A61K 47/06* (2013.01); *A61K 47/10* (2013.01); *A61P 17/00* (2018.01)

(58) Field of Classification Search
None
See application file for complete search history.

(56) References Cited

U.S. PATENT DOCUMENTS

| | | | |
|---|---|---|---|
| 6,440,437 B1 | 8/2002 | Krzysik et al. | |
| 7,357,923 B1 * | 4/2008 | Vasquez Lipi | A61K 9/0014 424/78.06 |
| 8,795,735 B1 | 8/2014 | Carter | |
| 10,016,466 B2 * | 7/2018 | Vasquez | A61K 35/06 |
| 2001/0003753 A1 | 6/2001 | Farber | |
| 2008/0193552 A1 | 8/2008 | Vasquez Lipi | |
| 2009/0162304 A1 * | 6/2009 | DiLeva | A61K 8/678 424/62 |
| 2012/0308670 A1 * | 12/2012 | Vazquez Lipi | A61K 9/0014 424/667 |

FOREIGN PATENT DOCUMENTS

WO 2010/082092 7/2010

OTHER PUBLICATIONS

U.S. Appl. No. 16/211,179, filed Dec. 2018, Vasquez, E.*
International Search Report issued for PCT/US2015/06055, of Record in U.S. Appl. No. 15/525,629.
Kubanov, et al. Modern methods of the treatment of hereditary epidermolysis bullosa. Vestnik Dermatologii I Venerologli, 2014, No. 6, pp, 47-56, English translation of Record in U.S. Appl. No. 15/525,629.
Written Opinion issued for PCT/US2015/06055, of Record in U.S. Appl. No. 15/525,629.
Extended European Search Report for EP 15860878.6, of Record in U.S. Appl. No. 15/525,629.

* cited by examiner

*Primary Examiner* — Michael Barker
(74) *Attorney, Agent, or Firm* — Neifeld IP Law, PC

(57) ABSTRACT

A composition and method for treating Epidermolisis bullosa (EB), comprising: applying to skin or mucosal surfaces of a patient in need of treatment for EB a dressing gauze or bandage without prior cleaning of said skin or mucosal surfaces, wherein distributed on said dressing is an effective amount of a composition containing beeswax; an oleaginous base, vitamins and a pharmaceutically acceptable excipient; then removing said dressing at least twice per day without damaging the patient's skin or mucosal surfaces due to removal of the dressing.

1 Claim, No Drawings

TOPICAL MEDICAMENT FOR SKIN AND MUCOSAL INJURIES

CROSS REFERENCE TO RELATED APPLICATIONS

This application is a continuation of U.S. application Ser. No. 15/525,629, filed May 10, 2017, which is a national stage entry of PCT/US2015/060555, filed Nov. 13, 2015, which claims priority to U.S. application No. 62/080,786, filed Nov. 17, 2014; and the preceding applications are incorporated herein by reference.

FIELD OF THE INVENTION

A topical ointment for treating skin injuries and mucous disorders.

BACKGROUND OF THE INVENTION

For purposes of this invention, the term "skin" is meant to refer to dermis and epidermis, as well as mucosal membranes.

Epidermolysis bullosa (EB) is an inherited connective tissue disease causing blisters in the skin and mucosal membranes after minor trauma, with an incidence of 1/50,000. It is a result of a defect in anchoring between the epidermis and dermis, resulting in friction and skin fragility. Its severity ranges from mild to lethal.

Epidermolysis bullosa simplex is a form of EB that causes blisters at the site of rubbing. It typically affects the hands and feet, and is typically inherited in an autosomal dominant manner, affecting the keratin genes KRT5 and KRT14.

Junctional epidermolysis bullosa is an inherited disease affecting laminin and collagen. This disease is characterized by blister formation within the lamina lucida of the basement membrane zone and is inherited in an autosomal recessive manner. It also presents with blisters at the site of friction, especially on the hands and feet, and has variants that can occur in children and adults.

Dystrophic epidermolysis bullosa (DEB) is an inherited variant affecting the skin and other organs. "Butterfly children" is the term given to those born with the disease, as their skin is seen to be as delicate and fragile as a butterfly's wings. DEB is caused by genetic defects (or mutations) within the human COL7A1 gene encoding the protein type VII collagen (collagen VII). DEB-causing mutations can be either autosomal dominant or autosomal recessive.

EB produces blisters or vesicles on the skin which contains serohematic fluid. When these blisters burst they produce injuries similar to burns that evolve, producing multiple scars and retractions of the skin which cause functional disabilities such as pseudosyndactyle, among others. Injuries also appear in membranes and mucosal membranes generating complications through the gastrointestinal tract which causes malnutrition, making healing even harder.

A characteristic of EB is the pronounced fragility of the skin and mucosal areas that lead to the formation of blisters and ulcers in response to minor traumas. The more exposed areas of skin are the ones affected by frequent friction or pressure. The peribuccal tissue, skin and mucous of lips or cheeks are specially affected because they are constantly exposed to chewing trauma. The ulcers produced in the peribuccal area during the chewing process generate scars and the tissues retract causing microustomya, until patients cannot open their mouths.

Even though the complete spectrum of clinical signs is wide: blisters, itching, skin erosions, atrophic scars, hyperqueratosis and ulcers are the main skin expressions of this disease.

Simple EB is diagnosed at birth; its main characteristic is the formation of blisters after a traumatic event, frequently in the palms of the hands, elbows, and soles of the feet. Blisters could be flaccid and when they burst they leave a melceric scab. Blisters are of erythematous base due to friction, and exacerbated by perspiration and excessive heat.

Joint EB presents blisters of generalized distribution, hyperplasic granulation tissue in the perioral, perinasal and groin regions or in the locations of the blisters. It affects the mucous of the mouth (intraoral vesicles) larynx, bronchus, esophagus, recto and vagina. Extended denudated areas in places of friction. Combination of chronic infections and loose of iron through the skin can turn into a chronic anemia.

Dystrophic EB presents blisters, either localized or generalized; when they disappear they leave dystrophic scars. Big denudated skin areas could be seen in places like the thorax. Blisters appear spontaneously in any place, being more frequent in friction areas. In addition, they could suffer from pseudosindactilia. Among complications they may suffer Espino cellularaggressive carcinoma. The formation of vesicles all over the body may result in the loss of body fluids, electrolytes, blood and proteins; dehydration, anemia and slow growth.

Known methods of treatment for EB are only partially effective. They focus on treating the pain and bacterial infections associated with injuries of the skin, but no definitive treatment exists today. The known treatments are symptomatic and palliative, focusing on preventing the development of injuries and their complications, e.g., draining blisters, using creams containing antibiotics, antiseptic agents and silicone patches. These prior art treatments do not provide a satisfactory therapeutic effect. For instance, when gauze dressings or silicone bandages are pulled off they may cause some harm to healthy skin around the wounds due to their adherence level, and leave suppuration in the area that must be removed by mechanical means (e.g., cleaning them with gauze), which slows the healing process.

Finding a treatment that can provide proper healing of the injuries produced by EB is a challenge that medical science has not achieved.

The present invention provides a non-toxic topical ointment based on natural ingredients which can provide high therapeutic efficiency for the injuries described above and diminish the many complications of EB.

A topical ointment for treating injuries and skin disorders is disclosed in U.S. Pat. No. 7,357,923 (Vasquez Lipi) for the treatment of a wide variety of skin injuries which is suitable for use on mucous surfaces. This ointment is composed of an oleaginous base, olive oil, sunflower oil, almond oil, castor oil, mineral oil and virgin beeswax as primary ingredients.

SUMMARY OF THE INVENTION

An object of the invention is to provide a composition for application to skin or mucosal surfaces of patients having Epidermolisis bullosa (EB), comprising:
about 15% to about 30% petroleum jelly,
about 5% to about 10% cod liver oil,
about 15% to about 30% beeswax,
about 5% to about 10% flax seed oil,
about 5% to about 10% grape seed oil, and
about 5% to about 10% chia oil, a pharmaceutically-acceptable excipient for topical application to the skin, and a preservative. Optionally, the composition may contain about 5 to 10% olive oil.

Another object of the invention is to provide a method for treating Epidermolisis bullosa (EB), comprising:
 a) applying to skin or mucosal surfaces of a patient in need of treatment for EB a dressing gauze or bandage without prior cleaning of said skin or mucosal surfaces, wherein distributed on said dressing is an effective amount of a composition containing: from about 15 to about 30 percent by weight of beeswax; an oleaginous base, an added vitamin selected from the group consisting of vitamin A, D and E; and a pharmaceutically acceptable excipient and a preservative;
 b) removing said dressing at least twice per day without damaging the patient's skin or mucosal surfaces due to removal of the dressing. The more often that the dressings are changed the faster the wounds heal.

It is important to understand that changing the dressings twice a day is only possible because of the ointment's benefits, i.e., there is no pain, and the gauze does not stick to the tissue. With prior art treatments the dressings are generally changed every two days, or else they give morphine to the patients to bear the pain of more frequent dressing changes.

DETAILED DESCRIPTION OF THE PREFERRED EMBODIMENTS

The present method of treatment can make use of the ointment disclosed in U.S. Pat. No. 7,357,923, which is incorporated by reference. However, an improved ointment formulation is disclosed herein for topical application to the skin of patients with EB who present blisters, ulcers, itching, skin erosions, atrophic or dystrophic scars, and friction areas where pseudosindactilia are found.

The expression "mucosal surfaces" as used herein includes the mucosal surfaces of buccal area and anal area as well as esophagus, nasal mucosal surfaces. The medicament comprises yellow beeswax (also known as virgin wax) preferably in an oleaginous base pharmaceutically acceptable for topical application to the skin and/or mucosal surfaces of the human body.

The topical medicament disclosed in U.S. Pat. No. 7,357,923 is a mixture of vegetable, animal and mineral oils which, combined in certain proportions, have been found to provide a topical medicament that leads to rapid healing of the blisters, vesicles, ulcers, of itching and pain.

The methods of the present invention are effective for treating dystrophic scars and retractions in the skin which lead to pseudosindactilia and microstomous. The disclosed methods reduce exudate formation and edema, help to clear skin wounds of necrotic tissue and purulent secretions, and encourage the appearance of granulation tissue and re-epithelization. These effects diminish the possibility of developing anemia by loss of secretions with hematic serum of the skin injuries in EB. The present medicament and method of application also possess anti-inflammatory, analgesic, antibacterial hemostatic and emollient properties.

Advantageously, the present method of treatment prevents bandages from adhering to wounds and so the treatment is painless, diminishing the use of analgesics to control pain, orally taken as well as intravenous like morphine. Frequent dressing changes serves to clean the wound of necrotic tissue and dirt, while the antibacterial effects of the ointment helps the skin to heal quickly, enhancing the natural immune defenses of the organ.

The present topical medicament also strengthens healthy skin due to its protective and emollient action, and therefore diminishes skin and mucous fragility which is found in EB. Due to this effect the frequency of blisters, vesicles and ulcers is also diminished. Protective action occurs in both hurt and healthy skin, and prevents harm from chemical, mechanical or physical (wind, friction, cold) irritative effects while diminishing odor and itching and while producing an anti-inflammatory effect.

The topical medicament of this invention forms an impermeable mask over the skin, prevents epidermal drying on conaceus stratus reducing water evaporation from skin surface, turning skin into a moisturized and elastic one.

In the intraoral region the topical ointment of this invention reduces the formation of blisters and vesicles mainly in the tongue and palate, the same as in the peribuccal region, being able to prevent atrophic healings so frequent in EB.

The topical ointments of the invention are able to treat locally the pain due to various and extended wounds of the skin and mucous areas so typical of EB starting from when these patients are born.

When treating am EB patient with a topical ointment of the invention, the ointment should be extended liberally on a gauze to be applied to the skin of the affected area. The dressing should never be unwoven cotton, it should be a gauze or net having small squares that let the skin breath. On top of the gauze a soft occlusive bandage should be placed. When the gauze is applied on the wound the gauze should cover a bigger area around the wound, preferably at least three centimeters extra all around. This bandaging process should be repeated at least twice a day with fresh gauze in the beginning and thereafter less often because of the good results with the treatment. Total duration of the treatment depends on the speed of the individual healing process.

Properties of the Present Invention:
 1. Decreases wound pain and provides relief to the patient, facilitating healing, and thus achieving increased patient autonomy.
 2. It increases the efficiency of healing, promoting the movement of epithelial tissue in the lesion.
 3. Provides a physiological moist environment.
 4. Prevents drying of the wound.
 5. Reduces infection rates in occlusion protects the wound, providing a bacterial barrier.
 6. Stimulates the formation of antimicrobial peptides.
 7. Promotes cell migration and promotes angiogenesis.
 8. Stimulates the synthesis of collagen and intercellular communication favors.

For minor wounds and healthy skin of EB patients the present topical ointment may be applied directly on the skin According to the present invention, for intraoral treatment of EB wounds like intrabuccal blisters and ulcers, the topical ointment is applied preferably on a gauze in the affected mucous and directly on minor wounds. Topical ointment should be extended on both sides of the gauze and can be placed on the tongue. When the tongue gets in touch with palate a double effect will be reached, it will be treating wounds in the tongue as well as in palate.

For the treatment of gynecological and proctologic conditions, the topical ointment of the present invention is applied using a variety of disposable virginally proctologic appliers easily fund in the market.

Due to the fact that the present ointment is applied in topical form, it is not usual to establish maximum and minimum doses. The amount of ointment to be applied should be related to the extension of the wound. For maximum benefit the wound should be completely covered by the topic ointment.

Very few of the present medicament's ingredients are absorbed by the skin or the mucous surface. Therefore, there are no secondary effects associated with the usage of the present topical medicament. Besides, the ingredients of the topical medicament are natural substances so they are well tolerated locally and systemically.

In one embodiment of the invention, the medicament comprises an oleaginous base of olive oil, sunflower oil, almond oil, cod liver oil, castor oil and virgin wax.

The preferred ointment of the invention comprises, as its primary ingredients, an oleaginous base of petroleum jelly (e.g., Vaseline), cod liver oil and virgin bee's wax, plus flax seed oil, grape seed oil and chia oil.

All embodiments of the invention can be combined with excipients commonly used in the preparation of topically-applied medicaments or cosmetic agents for application to the skin and/or mucosal surfaces of the human body, so as to provide, for example, a cream, gel, lotion or ointment. Preferably, the excipients provide emollient properties.

Preferred compositions according to the present invention contain from about 10 to about 50 percent by weight of virgin wax (yellow beeswax), based on the total weight of the formulation. Preferred compositions also contain Vitamins A, D and E, which can be provided from natural oleaginous sources or as synthetic additives.

In one embodiment, the invention provides a topical product for application to the skin comprising about 5% olive oil, about 21% sunflower oil, about 21% almond oil, about 10% cod liver oil, about 3% castor oil and about 23% beeswax, the balance of said product comprising a pharmaceutically-acceptable excipient for topical application to the skin.

In a preferred embodiment, the present invention provides a topical product for application to the skin comprising about 15% to about 30% petroleum jelly, about 5% to about 10% cod liver oil, about 15% to about 30% beeswax, plus 5% to about 10% flax seed oil, plus 5% to about 10% grape seed oil and 5% to about 10%/0 chia oil, the balance of said product comprising a pharmaceutically-acceptable excipient for topical application to the skin.

The oleaginous base of the ointment may be a mixture of vegetable and animal oils. Olive oil, almond oil, and castor oil are anhydrous vegetable oils made up of liquid or acid, fatty or saturated triglycerides. Olive oil is obtained from the ripe fruit of *Olea europaea* and its crop varieties. Sunflower oil is obtained from the seed/fruit of *Helianthus annus*, and is known to contain about 75 mg Vitamin E (mixed tocopherols) per 100 g. Almond oil is obtained from the seeds of *Prunus amygdalus*.

Cod liver oil is the oil obtained from the fresh livers of *Gadus morrhua* and other species of Gadidae.

The oil is extracted from the liver using steam, which breaks down the cellular membranes. Once obtained it is frozen and filtered to separate the stearin. Cod liver oil contains predominantly glycerides with non-saturated fatty acids that together comprise morrhuic acid. It also contains cholesterol, but the most important constituents are vitamins A and D, i.e., retinol and cholecalciferol or vitamin D3. Cod liver oil is known to contain at least about 850 U.S.P. units (255 .mu.g) of Vitamin A per gram, and at least about 85 U.S.P. units (2.125 µg) of Vitamin D per gram.

Castor oil is the cold-drawn oil of the seeds, stripped of the episperm, of Ricinuscommunis and other members of its family Euphorbisceae. It is a slightly yellow to colorless thick, viscous liquid with mild odor or odorless and subtle taste.

As used herein the term "virgin wax" or "yellow beeswax" refers to the product of fusion and purification of the honeycomb of the *Apis mellifera* (Apidae) bee after the honey has been separated. Preferably, the topical medicament contains between about 10 and about 50 percent by weight of yellow beeswax, more preferably between about 18 and about 27 percent, and even more preferably between about 23 and about 25 percent. Concentrations greater than about 50 percent by weight generally are not preferred because of the solid consistency of beeswax resulting in an undesirably high viscosity or hardness of the final product. Percentages are expressed throughout this application as percent by weight, based upon the total weight of the product, unless otherwise noted.

Flax seed oil, also known as linseed oil, is a colorless to yellowish oil obtained from the dried, ripened seeds of the flax plant (*Linum usitatissimum*, Linaceae). The oil is obtained by pressing, sometimes followed by solvent extraction. Flax-based oils are sought after as food because of their high levels of α-Linolenic acid (a particular form of omega-3 fatty acid).

Grape seed oil is pressed from the seeds of grapes, and is thus an abundant by-product of winemaking. Grape seed oil contains linoleic acid.

Some of the fatty acids that compose the grape seed oil enhance the beauty are palmitoleic, stearic linolenic, alpha, docosanoic, and icosanoicicosenoic. These fatty acids have many uses for the skin, helping to protect it from the sun, aid in the healing of wounds, reduce varicose veins. Some scientific studies have shown that its antioxidant properties are even greater than those of vitamin C and E, not to mention astringent and antiseptic properties which are good for skin repair. In addition, this oil helps in tissue regeneration. Its capacity to block moisture and repair tissue makes the grape seed oil is very useful and effective.

Chia oil is derived from seeds of *Salvia hispanica*, commonly known as chia, a species of flowering plant in the mint family, Lamiaceae, native to central and southern Mexico and Guatemala. Chia seeds contain a high content of Omega-3 oil (morethan salmon), this oil helps to increase the production of collagen, which acts as an anti-inflammatory agent. Omega-3 reduces the appearance of wrinkles and combat acne and other skin imperfections also gives a smooth, youthful look to it. The most important action of this oil is that it regulates hormones, this is very important because when ever we are victims of our stress hormones are thrown off and your skin may be the first to be affected.

*Potassium: This nutrient, like other components of chia seeds, regulates hormone levels, prevents inflammation and swelling of skin and improves our facial muscle activity from it.

Advantageously, the topical medicament of the invention contains Vitamins A, D and E. Synthetic versions of these vitamins can be added during formulation, or, preferably, the vitamins can be added via the inclusion of their natural sources, for example, cod liver oil and sunflower oil. The amounts of these vitamins can be varied, as can their sources. Preferred formulations of the medicaments can contain, per 100 g of the final formulation, between about 1275 and about 3825 µg Vitamin A, preferably about 2550 µg; between about 10.625 and about 31.875 µg Vitamin D, preferably about 21.25; and between about 975 and about 3000 mg Vitamin E, preferably about 2025 mg.

* Vitamin A and E: Vitamin E is known for its powerful antioxidant property that produces an anti-aging effect, which prevents wrinkles and fights skin inflammations. It is also used to treat acne scars or decrease the same as it accelerates cell regeneration. Vitamin A also acts as anti-inflammatory, anti-acne producing bacteria. This vitamin regulates the processes of the skin, helping to correct conditions of drying and dehydration, addition, like vitamin E assists in the rapid healing of wounds and protects the skin in general.

The excipients used in the topical medicament of the present invention are comprised primarily of emollients. Emollients are lipids or substances with a similar consistency which, when applied to the skin, protect and soften the skin, making it more supple. Emollients are used primarily as the excipients and bases of ointments and other dermatological preparations. A simple classification of emollients is as follows:

1) Oil-based: Oil-based emollients include fats. These products are anhydrous, do not absorb water and are insoluble in it, and are non-washable. Oil-based emollients include: a) hydrocarbons or mineral fats obtained by the distillation of petroleum (petroleum jelly, e.g., Vaseline); b) vegetable oils and liquid triglycerides; c) animal fats or solid natural triglycerides.

2) Absorbent bases: These bases are anhydrous and insoluble in water, and are hydrophilic. They typically form water-like emulsions in oil and, thus, can incorporate substances in aqueous solutions. In addition, they are largely non-washable. Absorbent bases include: a) Lanolin or wool fats that are obtained from sheep's wool and made up of fatty acids and cholesterol esters; and b) cetyl and stearyl alcohols, which are solid alcohols obtained by hydrogenation of their respective acids.

3) Emulsive bases: These bases absorb-water, but are insoluble in it, forming water emulsions in oil that are not very washable and can be easily removed from the skin. They include surface active agents (surfactants) which improve wetting of surfaces. They include: a) soaps or salts of fatty acids that may be acidic or basic depending on whether the lipophilic group is anionic or cationic; b) sulfated alcohols which are semi-synthetic substances; and c) synthetic surface active agents.

4) Water soluble bases: These bases are anhydrous, absorb water, and are completely soluble in water. They are also non-fatty and washable. For example, glycerin is obtained from fats and, due to its hydrophobicity, has the property of extracting water from the surface of the mucosa or denuded skin. It does not damage intact skin.

When applied to the skin, these substances, which are in general chemically inert, have a protective and emollient action. The protective action occurs on healthy and diseased skin and prevents the effects of chemical, mechanical, and physical (cold, wind) irritants while decreasing burning and pruritus and producing an anti-inflammatory effect. Since these substances form a more or less impermeable layer over the skin, they prevent drying of the epidermis over the stratum corneum by decreasing the evaporation of water from the cutaneous surface. Thus, the skin is softer and more supple. In this way, emollients mimic the natural sebaceous layer that covers normal skin. The bases envisioned for use in the present invention, including the water soluble ones, are well absorbed by the skin, but almost not at all by the epidermis or the sebaceous glands of the hair follicles.

In practicing the present invention, preferably the excipient is comprised of stearic acid and liquid petroleum jelly, with butylhydroxytoluene (BHT) as a preservative and, optionally, herbal essence.

Other excipients can be used in lieu of petroleum jelly, such as olive oil, cod liver oil and other natural oils, depending upon the ultimate consistency that is desired which, in turn, depends upon the ultimate use to which the product will be put. Additionally, other preservatives can be substituted for or used in combination with BHT.

Stearic acid is a mixture of solid fatty acids in variable proportions. It is an absorbent, anhydrous, and non-water soluble base which forms water-type emulsions in oil. When combined with the oil bases, stearic acid increases their consistency (viscosity) and makes them hydrophilic. As used herein, the term herbal essence refers to any of the well-known extracts of aromatic plants, such as an aromatic extract of chamomile.

The topical product of the instant invention, which can be in the form of, for example, a cream or an ointment, can be formulated as products specifically adapted for a variety of applications including skin, vaginal, and proctological creams/ointments. Regardless of the specific formulation and the environment in which the product is utilized, the topical product of the invention shows ability to stimulate granulation and re-epithelization and to act as an anti-pruritic surface analgesic and anti-inflammatory agent.

Once prepared, the topical medicament of the invention should be stored in a cool place to maximize its preservation. The final product can be packaged in, for example, 20 g. and 50 g. tubes, or in 50 g., 100 g., 200 g. and 500 g. jars.

The present invention is further described in the following Example, which is provided for illustrative purposes only and is not to be construed as limiting.

Example 1

In order to prepare a 100 g. sample of the topical medicament of the invention, the following ingredients were combined:

PRIMARY INGREDIENTS Olive oil 5.72 g Sunflower oil 21.72 g Almond oil 21.72 g Cod liver oil 10.72 g Castor oil 3.72 g Virgin wax 23.40 g EXCIPIENT BASE Stearic acid 2.0 g Herbal essence 0.980 g Butylhydroxytoluene 0.020 g Liquid petroleum jelly 10.0 g Preparation Step 1

The total quantities of the stearic acid and virgin wax are placed in a stainless steel receptacle outfitted with a double casing. The ingredients are heated to 65° C.-70° C. so that the solids melt.

Preparation Step 2

The melted mass is mixed and the total quantity of castor oil, olive oil, cod liver oil, almond oil, and sunflower oil is added to the mixture.

Preparation Step 3

The total quantity of buthylhydroxytoluene is dissolved in the herbal essence and added to the mixture from step 2.

Preparation Step 4

The total quantity of liquid petroleum jelly (or other medically acceptable excipient) is added and the mixture is mixed for 30 minutes while maintaining the heat and, then, cooling slowly with continuous shaking.

Example 2

Cleaning wounds is normally a critical first step for any treatment that does not use a composition of this invention.

A cleaning step is used in other treatments to improve the condition of the wound and reduce the risk of infection. However, using the inventive method this cleaning step is avoided. No cleaning is done before application of a bandage containing a composition of the invention, not even cleaning with physiological saline. The dressings described herein act as a wound cleanser. Do not dry the wound or press the dressing. Do not use antiseptics or skin cleansers for cleansing the wound because its cytotoxic power hurts the new tissue. Do not perform drag or pressure irrigation of wounds with any solution, not even saline The inventive method prevents bacterial growth without the cytotoxic effect of the usual antiseptics.

Do not perform debridements because bacterial content, necrotic debris and bleeding from the wound remains in the dressing after it is removed. Action of the inventive composition itself cleans the wound, without any need for aggressive measures that are typical of prior art treatments.

Example 3—Case Report

An approximately 6-month old female patient received treatment according to the present invention for three months. The baby has two heterozygous mutations, c.4007insG in exon 33 and c.8505insC in exon 115 of the COL7A1 gene. Both mutations are frameshift mutations and will lead to the premature termination codons p.Asp1336fsX22 and p.Val2836fsX12, respectively. The patient's mother is a heterozygous carrier of mutation c.8505insC and the patient's father is a heterozygous carrier of mutation c.4007insG. The patient's brother is not a carrier of either of these mutations. Compound heterozygosity for these two frameshift mutations in COL7A1 supports a clinical diagnosis of recessive dystrophic epidermolysis bullosa and the risk for recurrence in subsequent pregnancies is 25%. Identification of both parental mutations means that DNA-based prenatal diagnosis is feasible in the future, if indicated. With regards to the predicted phenotype in this affected individual, a generalised from of RDEB is likely (severe generalized or generalized-other). That said, one of the mutations does occur close to the 3' end of the gene (exon 115 of 118) and therefore if some truncated protein can be synthesized from this mutant allele, a slightly milder phenotype might result—but the diagnosis remains recessive dystrophic epidermolysis bullosa.

The parent's testimonies after 3 months treatment with ointment of the invention:
  Blister occurrence decreased significantly: frequency changed from having new blisters almost every day to just 1 every 25 days.
  Skin color also changed from necrotic maroon to an almost normal health color.
  Most affected areas also decreased.
  The blisters are now free of blood. This allowed our baby to be more happy and relaxed. She showed a dramatic change of mood.
  She is now free of bandages and she can crawl and put her body weight on the hands and knees without risk of blistering
  Since it is a non-toxic product, we feel more comfortable to freely administer it all over her body.
  We also treated her mouth with the product and we also observed a reduction in blister occurrences.
  Cures become more and more simple, thus reducing the healing time.
  Due to the ointment's properties, we can treat our baby just with one single product.
  We foresee a great potential of the product for the treatment of internal mucosal injuries.
  Although the hands healed faster than the feet, the ointment helped to strengthen the skin and make it more elastic.
  The lubricant effect of the product allows us to have more time to share games and have fun with our baby. Thanks to the medication we were able to take off the gloves from her hands and she feels comfortable to play with objects without problem. This is so important because this helped to develop her motor skills.

Indications

Ointments of the invention are for topical application to the skin of EB patients presenting blisters, sores, itching, skin erosions, dystrophicoratrophic scars, areas of friction and friction pseudosyndactylyin patients with and without skin lesions as well. In the oral mucosa, gastrointestinal mucosa and genital mucosa, in areas with lesions and also in healthy mucosa.

Topical Application

The ointments of the invention are applied topically, so it is not critical to set a maximum and minimum dose. The amount of the composition to be applied should be adapted to the extent of the injury. For maximum benefit, the lesion must be completely covered by the dressing.

In treatment of a patient presenting with EB, the ointment is spread in a thin layer on gauze which exceeds lesion by 2 to 3 cm. It is then placed over the affected area. A light occlusive bandage is applied covering the dressing. This regimen is repeated 2 times daily at the start of treatment achieving wound cleansing and adding oxygen to it. Then, the frequency diminishes as a result of a favorable course of treatment. In exchange the lesion swabs should not be affected, one should not clean debris or scrape the tissue. One gauze is replaced by another one without touching the injured skin. The total treatment time depends on how quickly the healing process progresses. In mild lesions and healthy skin of patients with EB, the ointment is applied directly to the skin.

For intraoral lesions themselves using EB as ampoules and intraoral ulcer, gauze carrying the inventive composition is applied to the affected mucosa and directly, without gauze into minor injuries. The ointment will be extended to both sides of the Cambridge type gauze and subsequently placed on the tongue. As the tongue is in contact with the palate, it achieves the dual purpose of treating injuries both in language and in palate.

The same type of dressing is used irrespective of:
Location of the lesion
Severity of injury
Amount of exudate
Presence of tunneling.
Skin perilesionated
Signs of infection Advantages
  Using active dressings. No use of topical antiseptics, etc.
  Prevents cellular dehydration. Thereby preventing skin dryness forming an impermeable layer thereon, reducing the evaporation of water from the skin surface. So does the skin softness and elasticity.
  Reduces time spent on wound care, thanks to the ease of use of the dressings.
  Promotes insulation.
  Reduces the level of pain. Reduces itching and burning
  Autolytic debridement.
  Faster healing and quality of the healed skin.

No dystrophic scarring and skin contractures that cause disabling effect spseudosyndactyly or microstomiain EB.

Reduces the formation of exudates and edema and helps clear skin wounds with necrotic tissue and purulent secretions, thus promoting the development of granulation tissue and re-epithelialization.

Promotes anti-inflammatory, analgesic, antibacterial, hemostatic and emollient action.

It does not stick to wounds therefore its use is painless, eliminating the use of pain medication.

Will not harm healthy skin but has a protective, emollient, thus decreases the fragility of the skin and mucosa observed in EB and in this sense also reduces blisters, vesicles and ulcers. The protective action happens in the diseased skin and healthy skin and prevents damage produced by the chemical irritant effects, mechanical or physical (shear, friction, cold, wind)

In the intraoral region reduces blisters and blisters on the tongue and palate primarily and in the perioral region preventing scarring producing atrophy, so characteristic of the EB.

It is biocompatible. Ointment components are natural substances, mixed vegetable, animal and mineral, with high protein and essential amino acids for healing. Thanks to this natural formula patients have excellent tolerance of of the present invention both locally and systemically, with no contraindications for use.

Protect the wound from external aggression

Removes dead tissue absorbing

Leave a minimum amount of waste in the lesion

Secure Grip

Adapts to difficult locations

Easy to apply and remove without pain.

Excellent cost benefit

The invention claimed is:

1. A method for treating epidermolysis bullosa (EB) comprising:
    a) applying to skin or mucosal surfaces of a patient in need of treatment for EB a dressing gauze or bandage without prior cleaning of said skin or mucosal surfaces, wherein distributed on said dressing is an effective amount of a composition containing: from about 15 to about 30 percent by weight of beeswax; petroleum jelly, cod liver oil, flax seed oil, grape seed oil, chia oil, an added vitamin selected from the group consisting of vitamin A, D and E; and a pharmaceutically acceptable excipient and a preservative;
    b) removing said dressing at least twice per day without damaging the patient's skin or mucosal surfaces due to removal of the dressing.

* * * * *